United States Patent [19]
Rindone et al.

[11] Patent Number: 5,371,245
[45] Date of Patent: Dec. 6, 1994

[54] RECOVERY OF TOCOPHEROLS FROM PLANT AND ANIMAL OILS

[75] Inventors: Renato R. Rindone, Fair Oaks; Der-Shing Huang, Folsom, both of Calif.

[73] Assignee: Aerojet General Corporation, Rancho Cordova, Calif.

[21] Appl. No.: 155,046

[22] Filed: Nov. 19, 1993

Related U.S. Application Data

[63] Continuation of Ser. No. 104,299, Aug. 9, 1993, abandoned.

[51] Int. Cl.$^5$ .................................................. C07D 311/72
[52] U.S. Cl. ............................................................ 549/413
[58] Field of Search ........................................... 549/413

[56] References Cited

U.S. PATENT DOCUMENTS

| | | |
|---|---|---|
| 2,263,550 | 11/1941 | Andrews . |
| 2,349,270 | 5/1944 | Hickman . |
| 2,568,202 | 9/1951 | Overhoff et al. . |
| 2,729,655 | 1/1956 | Miller et al. . |
| 3,108,120 | 10/1963 | Brown et al. . |
| 3,122,565 | 2/1964 | Kijima et al. . |
| 3,983,147 | 9/1976 | Senda et al. . |
| 4,550,183 | 10/1985 | Willging . |

OTHER PUBLICATIONS

Roussouw, S. D. and von Rudloff, E., "Wool Wax. II. Lime Saponification," *J. Appl. Chem.* 2 (Jun. 1952).

*Primary Examiner*—Nicky Chan
*Attorney, Agent, or Firm*—Townsend and Townsend Khourie and Crew

[57] ABSTRACT

Tocopherols are isolated from vegetable oil distillates and other saponifiable substances in which tocopherols are naturally present, by saponification in an alcoholic medium, followed by metathesis with a zinc halide. The resulting zinc salts of fatty acids are readily precipitated out of solution without mechanical granulation or the addition of powdering agents, leaving the tocopherols in alcoholic solution from which they are readily recovered. The sterols and glycerol are also recoverable for use in other applications.

15 Claims, No Drawings

RECOVERY OF TOCOPHEROLS FROM PLANT AND ANIMAL OILS

This is a continuation of application Ser. No. 08/104,299 filed Aug. 9, 1993abandoned.

This invention resides in the field of tocopherols (vitamin E) and other vitamins, and the extraction of these substances from naturally-occurring materials such as edible oils.

BACKGROUND OF THE INVENTION

The purification of edible oils includes various processing steps to remove substances which are detrimental to the quality of these oils. One of these steps is water vapor distillation, generally performed at temperatures of 180° C. to 220° C. and pressures of 4.6 to 15.2 mm Hg, in which volatiles, colored components and compounds which are odiferous and cause an unpleasant taste are separated from the oils. As the water vapor condenses, a liquid phase separates which is insoluble in water and essentially consists of free fatty acids, mono-, di- and triglycerides, tocopherols, and sterols. On cooling, this phase forms a material with a waxy consistency which is called vegetable oil distillate, or "VOD". A typical composition for soybean oil VOD is about 20% sterols (all percentages by weight), 10% tocopherols, 20% free fatty acids, and the remainder primarily mono-, di- and triglycerides. Among these components, the tocopherols, which exist in $\alpha$-, $\beta$-, $\gamma$-and $\delta$-forms, are of value because of their activity as vitamin E, a well-known anti-oxidizing agent. As a result, commercial processes exist for the recovery of tocopherols from VOD as well as from naturally occurring substances which are similar in composition to VOD, such as palm oil.

Prior art processes for separating tocopherols from VOD include esterification, saponification, direct solvent extraction, ion exchange resin chromatography, and direct distillation. Saponification is the preferred method since it produces alkali metal soap which, due to its insolubility in the solvent used in the process, can be separated from the dissolved tocopherols, thereby permitting recovery of the tocopherols in a form relative free from fatty acids and glycerides. The processes themselves are costly, however, and tocopherols are produced in low yield.

Of the saponification processes, the lime saponification process is the most widely used. Hickman, U.S. Pat. No. 2,349,270, discloses the use of slaked lime for the saponification followed by a granulation of the resulting lime soap mass and extraction of the tocopherols from the granulated material with ethyl ether. Andrews, U.S. Pat. No. 2,263,550, discloses saponification of VOD with sodium hydroxide, followed by metathesis (ion exchange) with calcium chloride to convert the sodium soaps to calcium soaps, from which the tocopherols and other unsaponifiable matter are then extracted with acetone.

The disadvantages of each of these processes is that the calcium soap is formed in a wide particle size distribution, ranging from fine particles to lumps. The result is a soap mass which is lumpy in form and from which the unsaponificable matter is difficult to extract. To permit the extraction to take place, the soap mass must be ground into particulate form, a process which entails a substantial capital investment. Even then, solvent consumption is high and the recovery of tocopoherols and other useful unsaponifiable matter such as sterols is low.

Grinding is avoided in the process disclosed by Brown, et al., U.S. Pat. No. 3,108,120, which uses calcium silicate as a powdering agent in combination with acetone to facilitate the separation of the soluble tocopherols and sterols from the insoluble soap mass. Unfortunately, this process requires a large amount of powdering agent which remains in the soap mass, and the effectiveness of the powdering agent is diminished if the moisture content of the soap mass is too high.

Other disclosures of potential relevance to this invention are the disclosures of Rossouw, et al., J. Appl. Chem. 2:335–8 (1952), and Senda, et al., U.S. Pat. No. 3,983,147, both of which address the saponification of wool wax. The potential relevance is the description of saponification itself, and in the case of Senda, et al., the metathesis performed subsequent to the saponification. Wool wax however is not believed to contain tocopherols.

The problems cited above as well as others encountered in tocopherol recovery are avoided in the present invention, which addresses the need for a simple, cost efficient, high yield process for the recovery of tocopherols from vegetable oil distillates and other similar sources.

SUMMARY OF THE INVENTION

It has now been discovered that the use of a zinc halide for the metathesis of a tocopherol-containing alcoholic saponification mixture causes the fatty acids to precipitate in a fine particulate form as zinc salts, leaving the tocopherols and other non-fatty acid components in the alcoholic solution which is readily separable from the precipitate. Thus, in accordance with the present invention, a saponifiable oil mixture, such as a vegetable oil distillate or any of various other kinds of naturally-occurring substances or substances derived from naturally-occurring substances, is saponified with an inorganic base in an alcoholic medium or a medium consisting of an alcohol-water mixture, then reacted with a zinc halide to precipitate the fatty acids as zinc salts. The zinc salts occur in a granular form with a relatively uniform particle size compared to their calcium salt counterparts. This permits them to be filtered off easily, leaving the tocopherols in the filtrate. The zinc halide thus offers a considerable advantage over the widely used calcium compounds of the prior art by permitting the separation and recovery of the tocopherols to take place in high yield without the need for mechanical granulation or the addition of powdering agents to induce the separation of the tocopherols and other dissolved materials from the precipitated material.

This and other advantages of the present invention will be apparent from the description which follows.

DETAILED DESCRIPTION OF THE INVENTION AND PREFERRED EMBODIMENTS

Oil mixtures to which the present invention is applicable include any of the wide variety of mixtures known in the industry and the literature on saponification and tocopherol recovery as containing both fatty acids and tocopherols. This includes oils and waxes of both plant and animal origin. Examples are vegetable oils and vegetable oil residues such as corn oil, wheat germ oil, safflower oil, peanut oil, sunflower oil, cottonseed oil, linseed oil, soybean oil, rapeseed oil and palm oil, and animal oils such as fish oil and wool wax. Vegetable oil distillates are preferred.

Since the reaction medium is either an alcoholic or aqueous-alcoholic medium, preferred zinc halides for use in the metathesis which follows the saponification reaction are zinc halides which are soluble in water and/or at least partially soluble in an alcohol. Zinc bromide, zinc iodide and zinc chloride are particularly preferred, with zinc chloride the most preferred. The zinc halide is preferably used in stoichiometric amounts relative to the fatty acid salt formed in the saponification.

The saponification and metathesis are preferably performed in the same solvent medium, primarily for purposes of convenience, and this medium may be any solvent which dissolves the tocopherols, and preferably other non-fatty acid substances present in the original oil mixture or formed by the saponification reaction, to permit recovery of these substances from the precipitated zinc salts of the fatty acid. Alcohols and alcohol/water mixtures are preferred. Preferred alcohols are methanol, ethanol, 1-propanol, 2-propanol, 1-butanol, t-butanol and 2-methyl-1-propanol. Methanol, ethanol and 1-propanol are particularly preferred as the alcohols, with methanol the most preferred.

Removal of the precipitated zinc salts from the reaction mixture, together with any excess undissolved zinc halide, is achieved by conventional means. Examples are simple filtration, vacuum filtration, centrifugation, and simple settling and decantation. No mechanical granulation is either required or desired, nor are any settling agents, powdering agents or other additives which are known or used in other multiphase systems as agents for enhancing the separation of a solid phase from a liquid phase. When sterols are present, removal of the zinc salts at elevated temperature, for example in excess of 50° C., and particularly in excess of 60° C., is preferred to prevent precipitation of the sterols. When filtration is performed at this elevated temperature, precipitation of the sterols in the filter cake is avoided. Any sterols remaining in solution in the filtrate can be precipitated by cooling the filtrate further. The types and amounts of sterols present vary widely with the source mixture. Examples are cholesterol, 7-dehydrocholesterol, ergosterol, campesterol, lanosterol, lumisterol, tachysterol, stigmasterol, β-sitosterol, asterosterol, aplysterol, avenasterol, verongulasterol and gorgosterol. The composition of sterols in soybean oil is approximately 53% β-sitosterol, 20% stigmasterol, 20% campesterol, and 3% avenasterol.

The liquid remaining after removal of the precipitated matter contains the alcohol solvent, the tocopherols dissolved in the alcohol, and any other liquid or dissolved substances present in the starting material or formed as products of the saponification reaction. In starting materials where the fatty acids are present as mono-, di-or triglycerides, the saponification reaction results in the formation of glycerol, which will then be present in the alcoholic solution. In starting materials where the fatty acids are present in acid form, the saponification reaction produces water, which will also be present in the alcoholic solution. Dissolved sterols may also be present.

The tocopherols in the alcoholic solution can be isolated from the sterols and any glycerol and water present by evaporation of the alcohol solvent to leave the solutes in the form of a cloudy oil mixture and a precipitate. The solutes are then redissolved in a solvent which predominantly or preferentially dissolves the tocopherols. Examples of such solvents are nonpolar aliphatic hydrocarbons, of which hexane is particularly preferred. The sterols are less soluble in such a solvent, and are readily isolated by filtration. Glycerol and water will form a separate liquid phase, and are readily isolated by decantation or any other form of liquid-liquid phase separation. The tocopherols are then readily recovered from the remaining solution by evaporation of the solvent, or purified by distillation. Alternatively, the cloudy oil mixture and precipitate remaining after the removal of the alcohol can be placed in a centrifuge to form separate layers of the liquid tocopherols, the aqueous glycerol solution, and the precipitated sterols. This eliminates the need for a second solvent.

The saponification reaction which precedes the zinc halide metathesis is conducted in a conventional manner, using an inorganic base in the alcoholic medium described above. Sodium hydroxide and potassium hydroxide are preferred, with sodium hydroxide particularly preferred. The base is conveniently dissolved in the alcoholic medium prior to being added to the oil mixture. The amount of base may vary, and the optimal amount for any particular VOD will depend on the saponification number of the VOD. For VOD's with saponification numbers ranging from about 100 to about 175 (expressed in mg KOH/g), optimal yields will be generally be obtained with at most about 0.500 equivalent of base per 100 g of the VOD. The most preferred level of base for this saponification number range is about 0.300 to about 0.500 equivalent per 100 g of VOD. Best results are further achieved when the saponification reaction is performed at reflux for at least about sixty minutes.

The following examples are offered for purposes of illustration, and are intended neither to limit nor to define the invention in any manner.

EXAMPLES

Example 1

A four-neck three-liter flask, fitted with a mechanical stirrer, a digital thermometer, a condenser, an addition funnel, a pH probe and a heating mantle, and supplied with a positive nitrogen atmosphere, was charged with NaOH (54.3 g, 1.36 moles) dissolved in 900 mL of methanol. To this solution was added a melted soybean oil distillate (324 g) in one portion. The soybean oil distillate, which was supplied by Archer Daniels Midland Company, Decatur, Ill., had a saponification number of 134 mg KOH/g, with a consistency like that of peanut butter and a melting point range of 50°–55° C. The distillate contained 9.61% (by weight) tocopherols, based on high performance liquid chromatography (HPLC) analysis. The combination of the methanolic caustic solution and the soybean oil distillate produced a brown slurry.

The slurry was heated to reflux (68°–70° C.) for 45 minutes. During reflux, the pH of the slurry was 9.4. After the 45 minutes of reflux, the heat supply to the heating mantle was turned off, and $ZnCl_2$ (99.4 g, 0.729 mole) dissolved in methanol (450 mL) was added over a period of seventeen minutes. The fatty acid zinc salt precipitated immediately upon the addition of the $ZnCl_2$. The reaction mixture was then chilled to ambient temperature and filtered. Filtration was complete in about 2 minutes, resulting in a wet filter cake which was yellow-brown in color and measured 2.5 inches (6.35 cm) in height and 5.2 inches (13.2 cm) in diameter. The filter cake was washed twice with 450-mL portions of methanol, then with water and dried. The resulting fatty acid zinc salt weighed 297.8 g.

The methanol filtrates were combined and stripped in vacuo to produce a cloudy oily mixture (160.9 g) which was then dissolved in 600 mL hexane. The result was a three-phase mixture consisting of a hexane layer, an aqueous glycerol layer, and solids. The solids (weighing 25.9 g and including the sterols content of the soybean oil distillate and the excess ZnCl$_2$) were filtered off first, followed by removal of the aqueous glycerol layer (61.9 g). The hexane layer was washed twice with 200-mL portions of deionized water, and stripped in vacuo to yield a brown liquid (concentrated tocopherols) weighing 56.5 g with a tocopherol content of 55.3% (by weight) as determined by HPLC, which corresponds to a recovery yield of 100.3%.

A 15.85-g portion of the crude tocopherol mixture was distilled by a Kugelrohr apparatus (<1 mm Hg, 160°–185° C.) to remove low boilers, 2.3 g. After distillation, the crude tocopherol mixture weighed 13.2 g with a tocopherol content of 83.9 area percent by gas chromatography and 62% by weight as determined by HPLC analysis. These results are listed in the table which follows these examples (Table II).

Examples 2 through 5

The next four experiments were conducted in a similar manner, using the same VOD at starting amounts of 107 g, 108 g, 108 g and 324 g, respectively, and varying amounts of caustic and zinc chloride relative to the VOD. In each experiment, the fatty acid zinc salt precipitated immediately upon addition of the sodium hydroxide, and was easily filtered off. In each case, filtration was complete in about 2 minutes. The results are listed in Table II below. It will also be noted from this data that the tocopherol yield increased sharply when the ratio of equivalents of NaOH per 100 g of the vegetable oil distillate was below 0.500, and that optimal yields were obtained when this figure was between 0.300 and 0.500.

Example 6

In this experiment, the same VOD was again used (565 g), but the reaction medium was a combination of methanol and water at a volume ratio of 95/5. The methanol was added by first dissolving the VOD in methanol prior to the addition of the caustic. The sodium hydroxide was then added as a 50% (by weight) aqueous solution, and the zinc chloride as a 70% aqueous solution (by weight). Here again, the zinc salt precipitated out readily, and was easily filtered off. The results from this experiment are also listed in Table II.

Example 7

In this experiment, a VOD with a lower tocopherol content was used. The VOD was supplied by Cargill, Inc., Minneapolis, Minn., and was unidentified as to biological source, but its tocopherol content was quoted as 6.7%, and its saponification number as 162 mg KOH/g. The amount used was 559 g. Methanol in combination with aqueous sodium hydroxide and aqueous zinc chloride were again used, for a methanol/water volume ratio of 95/5. After metathesis, the reaction mixture was filtered hot at 65°–70° C., and most of the sterols precipitated in the filtrate. The filtrate was then chilled to 0°–5° C., and the sterols were filtered out and isolated. The results from this experiment are listed in Table II.

Example 8

This example repeated the experiment of Example 7 with 613 g of the same VOD, using ethanol in place of the methanol, however. Similar results were obtained, however, and these are reported in Table II below.

Example 9

The procedure of Example 7 was followed, using 560 g of the VOD, except that after the methanol stripping, the resulting oily mixture (206.2 g) was separated into three layers using a solid bowl centrifuge. A complete separation of the mixture into layers was achieved in a short time. The top layer contained the tocopherols, the middle layer glycerol/water, and the bottom layer the sterols. The weights of the layers and the tocopherol area percent of each layer according to HPLC analysis, were as follows:

TABLE I

| Layer | Weight (g) | Tocopherol Content (%) |
|---|---|---|
| tocopherol | 36.6 | 56.92; 61.23 |
| glycerol/water | 89.7 | 0 |
| sterols | 79.9[a] | 5.25 |
| Total: | 206.2 | |

[a] including 28.5 g (dry basis)

The yields are reported in Table II.

Example 10

Comparative Example

This example is outside the scope of the invention, and is included for comparison to show the improvement achieved with zinc chloride. The experimental procedure was the same as that of Example 2, except that calcium chloride was used in the metathesis step in place of zinc chloride. The calcium soap thus formed was lumpy and the filtration required about 15 minutes to complete, whereas all other separations were completed in about 2 minutes. It is also evident from the data in Table II below that the yield of tocopherols was 16.4%, which is considerably lower than the yields obtained using zinc chloride as the metathesizing agent. This low tocopherol recovery yield is due to the difficulty in filtration. The major component of the crude tocopherols mixture after the stripping of methanol was the calcium salt of the fatty acid.

TABLE II

| | EXTRACTION OF TOCOPHEROLS FROM VEGETABLE OIL DISTILLATE (VOD) | | | | | | |
|---|---|---|---|---|---|---|---|
| Example No. | Saponification Medium (volume ratio) | equiv. NaOH per 100 g VOD | Salt Added For Metathesis type | (g) | Fatty Acid Salt Produced (g) | Tocopherol yield (%) | Sterols Isolated (g) |
| 1 | CH$_3$OH | 0.420 | ZnCl$_2$ | 99.4 | 297.8 | 100.3 | — |

TABLE II-continued
EXTRACTION OF TOCOPHEROLS FROM VEGETABLE OIL DISTILLATE (VOD)

| Example No. | Saponification Medium (volume ratio) | equiv. NaOH per 100 g VOD | Salt Added For Metathesis type | Salt Added For Metathesis (g) | Fatty Acid Salt Produced (g) | Tocopherol yield (%) | Sterols Isolated (g) |
|---|---|---|---|---|---|---|---|
| 2 | $CH_3OH$ | 0.255 | $ZnCl_2$ | 37.2 | 68.5 | 50.0 | — |
| 3 | $CH_3OH$ | 0.585 | $ZnCl_2$ | 85.5 | 112.7 | 9.2 | — |
| 4 | $CH_3OH$ | 0.420 | $ZnCl_2$ | 33.2 | 107.8 | 94.5 | — |
| 5 | $CH_3OH$ | 0.420 | $ZnCl_2$ | 99.5 | 323.4 | 92.5 | — |
| 6 | $CH_3OH/H_2O$ (95/5) | 0.309 | $ZnCl_2$ | 106.3 | 493.0 | 42.5 | 79.3 |
| 7 | $CH_3OH/H_2O$ (95/5) | 0.419 | $ZnCl_2$ | 159.6 | 521.2 | 70.7 | 144.3 |
| 8 | $C_2H_5OH/H_2O$ (95/5) | 0.419 | $ZnCl_2$ | 175.0 | 526.5 | 102.0 | 153.8 |
| 9 | $CH_3OH/H_2O$ (95/5) | 0.419 | $ZnCl_2$ | 159.5 | 523.5 | 63.1 | 119.5 |
| 10 (comparative) | $CH_3OH/H_2O$ (95/5) | 0.419 | $CaCl_2$ | 78.0 | 354.8 | 16.4 | 12.4 |

The foregoing is offered primarily for purposes of illustration. It will be readily apparent to those skilled in the art that the operating conditions, materials, procedural steps and other parameters of the system described herein may be further modified or substituted in various ways without departing from the spirit and scope of the invention.

What is claimed is:

1. A method for isolating a tocopherol fraction from an oil mixture containing at least one tocopherol and at least one fatty acid, said method comprising:
   (a) saponifying said oil mixture with an inorganic base to form a saponification mixture;
   (b) reacting said saponification mixture with a zinc halide to cause precipitation of a zinc salt of said at least one fatty acid, leaving a liquid solution containing said tocopherol fraction;
   (c) recovering said tocopherol fraction from said liquid solution.

2. A method in accordance with claim 1 in which said zinc halide is zinc chloride.

3. A method in accordance with claim 1 in which step (a) is performed in an alcoholic medium.

4. A method in accordance with claim 3 in which said alcoholic medium is a member selected from the group consisting of methanol, ethanol, 1-propanol, 2-propanol, 1-butanol, t-butanol and 2-methyl-1-propanol media.

5. A method in accordance with claim 3 in which said alcoholic medium is a methanol medium.

6. A method in accordance with claim 1 in which said oil mixture is a member selected from the group consisting of vegetable and animal oil distillates.

7. A method in accordance with claim 1 in which said oil mixture is a vegetable oil distillate.

8. A method in accordance with claim 7 in which said vegetable oil distillate has a saponification number of from about 100 mg KOH/g to about 175 mg KOH/g, and step (a) comprises contacting said vegetable oil distillate with at most about 0.500 equivalent of said inorganic base per 100 g of said vegetable oil distillate.

9. A method in accordance with claim 7 in which step (a) comprises contacting said vegetable oil distillate with from about 0.300 to about 0.500 equivalent of said inorganic base per 100 g of said vegetable oil distillate.

10. A method in accordance with claim 1 in which step (a) is performed at reflux for at least about 60 minutes.

11. A method in accordance with claim 1 in which said oil mixture further contains at least one sterol.

12. A method in accordance with claim 11 in which step (a) is performed in an alcoholic medium, said liquid solution of step (b) is an alcoholic solution, and step (c) comprises:
   (i) evaporating solvent from said alcoholic solution to leave an oil and solids mixture;
   (ii) combining said oil and solids mixture with hexane to form a multiphase mixture comprised of undissolved sterols and a hexane solution of said tocopherol fraction; and
   (iii) recovering said hexane solution from said multiphase mixture.

13. A method in accordance with claim 11 in which said saponification mixture contains glycerol.

14. A method in accordance with claim 13 in which step (a) is performed in an alcoholic medium, said liquid solution of step (b) is an alcoholic solution, and step (c) comprises:
   (i) evaporating solvent from said alcoholic solution to leave an oil and solids mixture;
   (ii) combining said oil and solids mixture with hexane to form a multiphase mixture comprised of undissolved sterols, a hexane solution of said tocopherol fraction, and a glycerol phase; and
   (iii) recovering said hexane solution from said multiphase mixture.

15. A method in accordance with claim 13 in which step (c) comprises:
   (i) evaporating solvent from said alcoholic solution to leave an oil and solids mixture;
   (ii) centrifuging said oil and solids mixture to form a three-phase mixture comprised of a tocopherol phase, a glycerol/water phase and a sterols phase; and
   (iii) recovering said tocopherol phase from said multiphase mixture.

* * * * *